(12) United States Patent
Raber et al.

(10) Patent No.: US 11,072,568 B2
(45) Date of Patent: *Jul. 27, 2021

(54) SOLVENT-FREE PROCESSING, SYSTEM AND METHODS

(71) Applicant: Scientific Holdings, LLC, Monrovia, CA (US)

(72) Inventors: Jeffrey Charles Raber, Pasadena, CA (US); Sytze Elzinga, Denver, CO (US)

(73) Assignee: Scientific Holdings, LLC, Monrovia, CA (US)

(*) Notice: Subject to any disclaimer, the term of this patent is extended or adjusted under 35 U.S.C. 154(b) by 79 days.

This patent is subject to a terminal disclaimer.

(21) Appl. No.: 15/676,744

(22) Filed: Aug. 14, 2017

(65) Prior Publication Data

US 2018/0016203 A1   Jan. 18, 2018

Related U.S. Application Data

(62) Division of application No. 14/537,341, filed on Nov. 10, 2014, now Pat. No. 9,732,009.

(60) Provisional application No. 61/902,388, filed on Nov. 11, 2013.

(51) Int. Cl.
    *C07B 63/00* (2006.01)
    *C07D 311/80* (2006.01)

(52) U.S. Cl.
    CPC ............ *C07B 63/00* (2013.01); *C07D 311/80* (2013.01)

(58) Field of Classification Search
    CPC .............................. C07B 63/00; C07D 311/80
    See application file for complete search history.

(56) References Cited

U.S. PATENT DOCUMENTS

| 9,732,009 B2* | 8/2017 | Raber ................... | C07D 311/80 |
| 2005/0266108 A1* | 12/2005 | Flockhart ............. | C07D 311/80 424/774 |
| 2012/0095087 A1* | 4/2012 | Hyatt ..................... | A61K 31/05 514/454 |

FOREIGN PATENT DOCUMENTS

| EP | 1 536 810 B1 | 8/2012 | |
| JP | 2006-320308 A | 11/2006 | |
| WO | WO-2010120939 A2 * | 10/2010 | ............. C12N 13/00 |

OTHER PUBLICATIONS

Skunk Pharm Research, LLC. "Extracting With Oils and Fats." (c) Apr. 1, 2012. Available from: < http://web.archive.org/web/20120401223549/http://skunkpharmresearch.com/extracting-with-oils-and-fats/ >. (Year: 2012).*

Takeda, S., et al. "Cannabidiolic acid, a major cannabinoid in fiber-type cannabis, is an inhibitor of MDA-MB-231 breast cancer cell migration." (Nov. 15, 2012). vol. 214(3), pp. 314-319. (Year: 2012).*

Massi, P. et al. "Antitumor Effects of Cannabidiol, a Nonpsychoactive Cannabinoid, on Human Glioma Cell Lines." J. Pharmacology and Experimental Therapeutics. (2004), vol. 308 (3), pp. 838-845. (Year: 2004).*

Skunk Pharm Research, LLC. "Extracting With Oils and Fats." (Apr. 1, 2012). Available from: < http://web.archive.org/web/20120401223549/http://skunkpharmresearch.com/extracting-with-oils-and-fats/ >. (Year: 2012).*

"EP Screw Press for Solvent Recovery, Hemp Processing." Available Oct. 4, 2008. Accessed Mar. 16, 2020. Available from: <https://www.presstechnology.com/dewatering-equipment-press-technology/ >. (Year: 2008).*

International Search Report for PCT/US2014/064860 dated Feb. 25, 2015 (4 pages).

Cannabidiol (CBD) Pre-Review Report Agenda Item 5.2, Expert Committee on Drug Dependence, Thirty-ninth Meeting, Geneva; Nov. 6-10, 2017, World Health Organization.

International Search Report dated Feb. 25, 2015, PCT/US2014/064860, 4 pages.

Jung, Julia et al, Detection of Δ9-tetrehydracannabinolic acid A in human urine and blood serum by LC-MS/MS, Journal of Mass Spectrometry, 2007; 42: 354-360, published online Jan. 12, 2007 in Wley InterScience DOI: 10.1002/jms.1167.

Massi, Paola, et al, Antitumor Effects of Cannabidiol, A Nonpsychoactive Cannabinoid, on Human Glioma Cell Lines, The Journal of Pharmacology and Experimental Therapeutics, Copyright 2004 by The Amencan Society for Pharmacology and Experimental Therapeutics JPET 308:838-645; 2004. vol. 308. No. 3, 61002/1126479.

Cannabidiol (CBD) Pre-Review Report Agenda Item 5.2, Expert Committee on Drug Dependence Thirty-Ninth Meeting, Geneva, 6-10, Nov. 2017, World Health Organization.

Takeda, Shuso, et al. Cannabidiolic acid, a major cannabinoid in fiber-type cannabis, is an inhibitor of MDA-MB-231 breast cancer cell migration, National Institute of Health, Tocxicol Lett. Nov. 15, 2012; 204(3): 314-319, doi: 10.1016/j-toxlet.2012.08.029.

Usami, Atsushi, et al. Characterization of Aroma-active Compounds in Dry Flower of *Malva sylvestris* L. by GC-MS-O Analysis and OAV calculations, Journal of Oleo Science, J. Oleo Sci. 62, (8) 563-570 (2013).

* cited by examiner

*Primary Examiner* — John Mabry

(74) *Attorney, Agent, or Firm* — J D Harriman; Foundation Law Group

(57) ABSTRACT

Disclosed is a process for purifying one or more chemical constituents from plant matter using extraction with a fluid that is not a solvent, for example, with a vegetable oil. The extracted chemical constituents may then optionally be further processed by heating in order to induce desired chemical transformations. The extracted chemical constituents are also processed by concentrating at reduced pressure, for example, by distillation.

16 Claims, 4 Drawing Sheets

SOLVENT-FREE PROCESSING, SYSTEM AND METHODS

CROSS REFERENCE TO RELATED APPLICATION

This application is a divisional of Ser. No. 14/537,341, filed Nov. 10, 2014, which claims priority to U.S. Provisional Patent Application No. 61/902,388, filed Nov. 11, 2013, the entire contents of which are incorporated herein by reference.

FIELD OF THE DISCLOSURE

The present disclosure relates to systems and methods for solvent-free processing of plant materials. The system and methods may use other materials, in place of a solvent, such as oil or an ionic liquid, for extracting plant material or for further extraction of a plant extract, followed by purification by distillation, optionally with heat-induced chemical transformation of natural products in the plant material. The heat-induced chemical transformation can include decarboxylation.

BACKGROUND OF THE INVENTION

Natural products encompass chemicals and chemical compositions derived from plants, animals, fungi, and microorganisms (see, e.g., Newman and Cragg (2012) J. Natural Products, 75:311-335). Natural products include taxanes, such as paclitaxel, which is renowned for use in treating cancer (Heinig and Jennewein (2009) African J. Biotech. 8:1370-1385). Natural products also include terpenes, which include aromatic compounds, such as limonene, menthol, eugenol, and beta-caryophyllene, which are used in foods and perfumes. Analogues of natural products have also found commercial use, and these include Warfarin, an analogue of the natural product, coumarin (Link (1959) Circulation. 19:97-107), and fingolimod, derived from a natural product made by the fungus *Isaria sinclairii*, and which is used to treat multiple sclerosis (Chiba and Adachi (2012) Future Med. Chem. 4:771-781).

Administered cannabinoids, as provided by non-purified sources or by partially purified sources, have found use in reducing the symptoms of various diseases. For example, administered cannabinoids have been found to reduce the spasticity, neuropathic pain, and tremors of multiple sclerosis (Leussink et al (2012) Ther. Adv. Neurol. Disord. 5:255-266; Lakhan and Rowland (2009) BMC Neurology. 9:59 (6 pages)). Moreover, cannabinoids can relieve chronic neuropathic pain (Ware et al (2010) Canadian Med. Assoc. J. 182:E694-E701; Grant et al (2012) Open Neurology J. 6:18-25; Lynch and Campbell (2011) Brit. J. Clin. Pharmacol. 72:735-744). The present disclosure fulfills an unmet need by providing concentrated preparations of purified cannabinoids that do not contain solvent, and that were not prepared using any solvent.

Some methods of preparing chemical compounds from plant material are known in the art e.g., U.S. Pat. No. 7,700,368, to Flockhart et al.; U.S. Pat. No. 8,846,409, issued Sep. 30, 2014, to Flockhart et al.; and European Patent Serial No. 1 536 810 B1 to Whittle et al.; the contents of all of which are incorporated by reference herein in their entirety). Methods of decarboxylating cannabinoids are also known (see U.S. Patent Publication Serial No. 2012/0046352 to Hospodor, the contents of which are incorporated by reference herein in their entirety).

SUMMARY

Briefly stated, the present disclosure comprises a process for purifying chemicals from plant matter using extraction with a fluid that is not a solvent, for example, with a vegetable oil. The extracted chemicals are then further processed by heating in order to induce a chemical transformation, which may be decarboxylation of extracted carboxylic acids. The extracted chemicals are also processed by concentrating at reduced temperature and pressures, for example, by distillation.

Systems and methods of the present disclosure are particularly useful for purifying chemicals such as tetrahydrocannabinolic acid (THCA), cannabidiolic acid (CBDA), and cannabigerolic acid (CBGA); and decarboxylating them to tetrahydrocannabinol (THC), cannabidiol (CBD), and cannabigerol (CBG), respectively.

A solvent is a substance that dissolves a solute, resulting in a solution. A solution has a single phase wherein the solvent and solute form complexes. This situation differs from non-solution mixtures wherein the compounds are insoluble, such that a residue remains. In a solution, the compounds are uniformly distributed at a molecular level, and no residue remains. A compound may be defined as a non-solvent in relation to another compound that cannot dissolve into it. For example, canola oil is a non-solvent of THC. The present disclosure includes the use of a variety of non-solvents, such as oils or ionic liquids.

The present disclosure provides a method for purifying one or more chemical constituents from plant matter comprising the steps of: (i) contacting the plant matter with a non-solvent; (ii) allowing chemical constituents from the plant matter to dissociate from the plant matter and to disperse into the non-solvent, thereby producing extracted plant matter and producing a non-solvent enriched in the chemical constituents; (iii) separating the extracted plant matter from the non-solvent enriched in the chemical constituents; and (iv) volatilizing at least one of the chemical constituents by one or more of heat, vacuum, or heat and vacuum, and (v) collecting the volatilized chemical constituents, wherein the collected volatilized chemical constituents is defined as the final product.

Also provided is the above method, wherein the non-solvent that is enriched in chemical constituents contains one or more of 6,10,14-trimethyl-2-pentadecanone, octacosane, hentriacontane, and eicosane, wherein the content of 6,10,14-trimethyl-2-pentadecanone, octacosane, hentriacontane, and eicosane, is defined as 100 percent (100%), and wherein the content in the final product of each of the one or more of 6,10,14-trimethyl-2-pentadecanone, octacosane, hentriacontane, and eicosane, is less than 50%.

In another aspect, the content in the final product of 6,10,14-trimethyl-2-pentadecanone is less than 80%, less than 70%, less than 60%, less than 50%, less than 40%, less than 30%, less than 20%, less than 10%, less than 5%, less than 2%, less than 1%, and so on.

In another aspect, the content in the final product of octacosane is less than 80%, less than 70%, less than 60%, less than 50%, less than 40%, less than 30%, less than 20%, less than 10%, less than 5%, less than 2%, less than 1%, and so on.

In another aspect, the content in the final product of hentriacontane is less than 80%, less than 70%, less than 60%, less than 50%, less than 40%, less than 30%, less than 20%, less than 10%, less than 5%, less than 2%, less than 1%, and so on.

In another aspect, the content in the final product of eicosane, is less than 80%, less than 70%, less than 60%, less than 50%, less than 40%, less than 30%, less than 20%, less than 10%, less than 5%, less than 2%, less than 1%, and so on.

What is further contemplated is the above method, wherein the non-solvent enriched in the chemical constituents comprises heat-decarboxylatable chemical constituents; that further includes the step of exposing to heat conditions that are sufficient to provoke heat-induced decarboxylation of at least some of the heat-decarboxylatable chemical constituents.

Also embraced is the above method that further includes the step of exposing the one or more chemical constituents to heat conditions that are sufficient to provoke heat-induced decarboxylation of at least some of the heat-decarboxylatable chemical constituents, wherein the heat conditions is more than 100° C., more than 98° C., more than 96° C., more than 94° C., more than 92° C., more than 90° C., more than 88° C., more than 86° C., more than 84° C., more than 82° C., more than 80° C., and so on.

Additionally, what is provided is the above method wherein the volatilization is conducted at a temperature that is more than 100 degrees C., more than 98° C., more than 96° C., more than 94° C., more than 92° C., more than 90° C., more than 88° C., more than 86° C., more than 84° C., more than 82° C., more than 80° C., and so on.

Also provided is the above method, wherein the non-solvent that is enriched in the chemical constituents is not processed by contacting with an inert matrix.

Also provided is the above method that does not comprise adding solvent in Step (i).

Also provided is the above method, wherein the chemical constituents comprise one or more cannabinoids.

Also provided is the above method, wherein the chemical constituents do not comprise a cannabinoid.

Also provided is the above method, wherein the plant matter is a cannabaceae, or is derived from a cannabaceae.

Also provided is the above method, wherein the non-solvent that is enriched in the chemical constituents comprises a first chemical constituent and a second constituent, and wherein the step of volatilizing results in a volatilized fraction, and also results in the separation of the first chemical constituent from the second chemical constituent, wherein the volatilized fraction is relatively enriched in the first chemical constituent and relatively depleted in the second chemical constituent.

Also provided is the above method, wherein the non-solvent that is enriched in the chemical constituents comprises a first chemical constituent and a second constituent, wherein the step of volatilizing results in a volatilized fraction, and also results in the separation of the first chemical constituent from the second chemical constituent, wherein the volatilized fraction is relatively enriched in the first chemical constituent and relatively depleted in the second chemical constituent, and wherein the non-solvent that is enriched in the chemical constituents contains heat-decarboxylatable chemical constituents, and wherein the step of volatilization results in heat-induced decarboxylation of less than about 5% of the heat-decarboxylatable chemical constituents.

In yet another aspect, what is provided is the above method, wherein the non-solvent that is enriched in the chemical constituents comprises a first chemical constituent and a second constituent, and wherein the step of volatilizing results in a volatilized fraction, and also results in the separation of the first chemical constituent from the second chemical constituent, wherein the volatilized fraction is relatively enriched in the first chemical constituent and relatively depleted in the second chemical constituent, and wherein the non-solvent that is enriched in the chemical constituents contains heat-decarboxylatable chemical constituents, and wherein the step of volatilization results in heat-induced decarboxylation of less than about 10% of the heat-decarboxylatable chemical constituents.

Moreover, what is provided is the above method, wherein the step of separating the extracted plant matter from the non-solvent that is enriched in the chemical constituents comprises one or more of (a) Centrifuging or filtering; or (b) Drawing hot gas through the non-solvent that is enriched in chemical constituents in order to volatilize and remove at least some of the chemical constituents.

Also provided is the above method, wherein the step of separating the extracted plant matter from the non-solvent that is enriched in the chemical constituents comprises drawing hot gas through the non-solvent that is enriched in chemical constituents in order to volatilize and remove at least some of the chemical constituents, followed by condensing the volatilized and removed chemical constituents to generate and collect a composition that comprises one or more condensed constituents. Also provided is the above method, wherein the step of exposing the chemical constituent to heat conditions that are sufficient to provoke heat-induced decarboxylation of at least one of the heat-decarboxylatable chemical constituent is conducted: during Step (ii); during Step (iii) with the proviso that Step (iii) comprises drawing hot gas through the non-solvent that is enriched in compound or chemical; or after Step (iii) but before Step (iv). In another aspect, the heat conditions are sufficient to provoke decarboxylation of at least two of the heat-decarboxylatable chemical constituents, at least three of the heat-decarboxylatable chemical constituents, at least wherein Step (iv) comprises a partial vacuum that increases volatilization of at least some of the chemical constituents from the non-solvent.

Also provided is the above method, wherein Steps (i-iv) are conducted continuously, and wherein the rate of each step is individually controlled to allow Steps (i-iv) to allow continuous operation, and to prevent substantial accumulation of partially processed chemical constituents from in between any given two adjacent two steps.

Also provided is the above method, wherein the plant matter comprises cannabaceae that is one or more of dried, chopped, ground, or powdered.

Also provided is the above method, wherein extraction with the non-solvent is batchwise.

Also provided is the above method, wherein extraction with the non-solvent is continuous and not batchwise.

Further provided is the above method, wherein the non-solvent comprises a vegetable oil, fruit oil, seed oil, nut oil, fish oil, wax oil, or a mixture of said oils.

Also provided is the above method, wherein the non-solvent comprises a vegetable oil that is canola oil, sunflower oil, safflower oil, or corn oil, or a mixture of one or more of said vegetable oils.

Also provided is the above method, wherein the non-solvent comprises a nut oil that is peanut oil, walnut oil, or almond oil, or a mixture of one or more of said nut oils.

Also provided is the above method, wherein the non-solvent comprises an ionic liquid, such as tributylmethylammonium methyl sulfate, or an imidazolium salt such as 1-butyl-3-methylimidazolium chloride.

Also provided is the above method, wherein the step of extracting does not include any solvent in an amount (concentration) sufficient to be effective in promoting extraction of the chemical constituents from the plant matter.

In system embodiments, what is provided is a system that is capable of carrying out a method for purifying one or more chemical constituents from plant matter comprising the steps of: (i) Contacting the plant matter with a non-solvent; (ii) Allowing chemical constituents from the plant matter to dissociate from the plant matter and to disperse into the non-solvent, thereby producing extracted plant matter and producing a non-solvent enriched in the chemical constituents; (iii) Separating the extracted plant matter from the non-solvent enriched in the chemical constituents; and (iv) Volatilizing at least one of the chemical constituents by one or more of heat, vacuum, or heat and vacuum, and (v) Collecting the volatilized chemical constituents, wherein the collected volatilized chemical constituents is defined as the final product; wherein the non-solvent enriched in the chemical constituents comprises heat-decarboxylatable chemical constituents; that further includes the step of exposing to heat conditions that are sufficient to provoke heat-induced decarboxylation of at least some of the heat-decarboxylatable chemical constituents, wherein the system comprises an extractor, a vacuum pump, an evaporator, a non-solvent for use in extracting plant matter, and a heating unit that is configured for heat-induced decarboxylation of a decarboxylatable chemical constituents. Also provided is the above system, wherein the non-solvent comprises a vegetable oil. Also provided is the above system, wherein the heating unit comprises one of: (i) a hot gas that is drawn through a composition comprising the chemical constituents and the non-solvent; (ii) a heating unit that is configured to heat the chemical constituents and volatilize evaporable chemical constituents, but that does not heat the chemical constituents by drawing hot gas through the composition comprising the chemical constituents and the non-solvent.

The following specifically concerns cannabinoids. What is provided is a method for purifying one or more cannabinoids from plant matter comprising the steps of: (i) Contacting the plant matter with a non-solvent; (ii) Allowing cannabinoids from the plant matter to dissociate from the plant matter and to disperse into the non-solvent, thereby producing extracted plant matter and producing a non-solvent that is enriched in the cannabinoids; (iii) Separating the extracted plant matter from the non-solvent that is enriched in the chemical constituent; and (iv) Concentrating the cannabinoids by distilling.

What is provided is the above method, that further includes the step of exposing the one or more cannabinoids to heat conditions that are sufficient to provoke heat-induced decarboxylation of at least some of the decarboxylatable cannabinoids. What is also provided is the above method, that excludes solvent from Step (i). What is provided is the above method, wherein the plant matter is derived from a cannabaceae. What is embraced is the above method, wherein the step of separating the extracted plant matter from the non-solvent that is enriched in the cannabinoids comprises one or more of: (a) Centrifuging or filtering; or (b) Drawing hot gas through the non-solvent that is enriched in chemical constituent in order to volatilize and remove at least some of the cannabinoids.

What is further contemplated is the above method, wherein the step of exposing the cannabinoid to heat conditions that are sufficient to provoke heat-induced decarboxylation of at least some of the decarboxylatable cannabinoids is conducted: during Step (ii); during Step (iii) with the proviso that Step (iii) comprises drawing hot gas through the non-solvent that is enriched in cannabinoid; or after Step (iii) but before Step (iv). Further provided is the above method, wherein Step (iv) comprises rotary evaporation or bulk distillation. Also embraced is the above method, wherein Step (iv) does not comprise bulk distillation.

Additionally contemplated is the above method, wherein Step (iv) comprises a partial vacuum that increases volatilization of at least some of the chemical constituents from the non-solvent. Also provided is the above method, wherein Steps (i-iv) are conducted continuously, and wherein the rate of each step is individually controlled to allow Steps (i-iv) to allow continuous operation, and to prevent substantial accumulation of partially processed chemical constituents from accumulating in between any given two adjacent two steps.

Also provided is the above method, wherein the plant matter comprises cannabaceae that is one or more of dried, chopped, ground, or, powdered. Further embraced is the above method, wherein extraction with the non-solvent is batchwise. Also provided is the above method, wherein extraction with the non-solvent is continuous and not batchwise.

What is further provided is the above method, wherein the non-solvent comprises a vegetable oil, fruit oil, seed oil, or a nut oil. Provided is the above method, wherein the non-solvent comprises a vegetable oil that is canola oil, sunflower oil, safflower oil, or corn oil, or a mixture of one or more of said vegetable oils. Provided is the above method, wherein the non-solvent comprises a nut oil that is peanut oil, walnut oil, or almond oil, or a mixture of one or more of said nut oils. Also provided is the above method, wherein the non-solvent comprises an ionic liquid, such as tributylmethylammonium methyl sulfate. Also provided is the above method, wherein the step of extracting does not include any solvent in an amount (concentration) sufficient to be effective in promoting extraction of the chemical constituent from the plant matter.

In systems embodiments, what is provided is a system that is capable of carrying out the above method, wherein the system comprises an extractor, a vacuum pump, an evaporator, a non-solvent, and a heating unit that is configured for heat-induced decarboxylation of a decarboxylatable chemical constituent. Also provided is the above system, wherein the non-solvent is a vegetable oil. Further provided is the above system, wherein the heating unit comprises one of: (i) a hot gas that is drawn through a composition comprising the chemical constituent and the non-solvent; (ii) a heating unit that is configured to heat the chemical constituent and volatilize evaporable chemical constituents, but that does not heat the chemical constituents by drawing hot gas through the composition comprising the chemical constituent and the non-solvent.

Methods of continuous operation that prevent accumulation of partially-processed, or partially-purified chemical constituent at any given intermediate step are provided, as follows. What is embraced is the above method, wherein Steps (i-iv) are conducted continuously, and wherein the rate of each step is individually controlled to allow Steps (i-iv) to allow continuous operation, and to prevent substantial accumulation of partially processed chemical constituents from accumulating in between any given two adjacent two steps.

Also embraced is the above method, wherein Steps (i-v) are conducted continuously, and wherein the rate of each step is individually controlled to allow Steps (i-v) to allow continuous operation, and to prevent substantial accumulation of partially processed chemical constituents from accumulating in between any given two adjacent two steps.

In embodiments, the present disclosure also provides the above method wherein the plant matter comprises one or more of dried *cannabis*, powdered *cannabis*, chopped *cannabis*, or ground *cannabis*. Also provided is the above method, wherein extraction with the non-solvent is batchwise. Also contemplated is the above method, wherein extraction with the non-solvent is continuous and not batchwise. Further provided is the above method, wherein the non-solvent comprises a vegetable oil or a nut oil. Additionally provided is the above method, wherein the non-solvent comprises a vegetable oil that is canola oil, sunflower oil, safflower oil, or corn oil, or a mixture of one or more of said vegetable oils. In yet another aspect, what is provided is the above method, wherein the non-solvent comprises a nut oil that is peanut oil, walnut oil, or almond oil, or a mixture of one or more of said nut oils. Also provided is the above method, wherein the non-solvent comprises an ionic liquid, such as tributylmethylammonium methyl sulfate. Also provided is the above method, wherein the step of extracting does not include any solvent in an amount (concentration) sufficient to be effective in promoting extraction of cannabinoids from the plant matter.

In a system embodiment, what is provided is a system that is capable of carrying out the above method, wherein the system comprises an extractor, an evaporator, a non-solvent, and a heating unit that is configured for heat-induced decarboxylation of cannabinoids. Also provided is the above system, wherein the non-solvent is a vegetable oil. Also provided is the above method, wherein the non-solvent comprises an ionic liquid. Moreover, what is embraced is the above system, wherein the heating unit that is configured for heat-induced decarboxylation of cannabinoids comprises one of: (i) a hot gas that is drawn through a composition comprising cannabinoids and a non-solvent; (ii) a heating unit that does not heat the cannabinoids by drawing hot gas through the composition comprising cannabinoids and a non-solvent.

DETAILED DESCRIPTION

Figure 1:
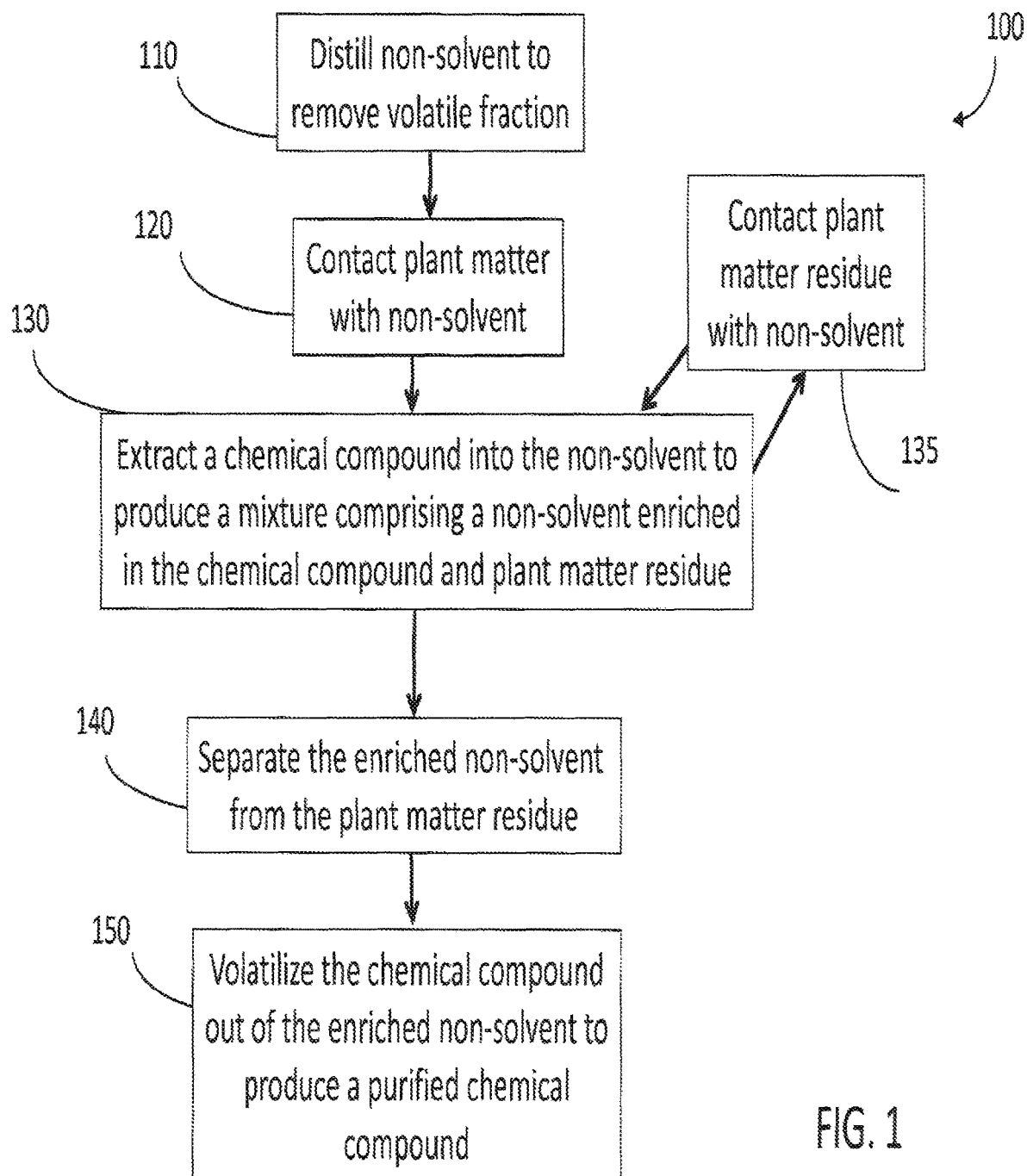
FIG. 1 shows a method of purifying a chemical compound from plant matter.

The present disclosure encompasses all possible combinations of the above embodiments, and encompasses all possible disclosures of each independent claim with its dependent claims. For example, what is encompassed is an invention that is the combination of Claim 1+Claim 2; or the combination of Claim 1+Claim 2+Claim 3; or the combination of Claim 1+Claim 3+Claim 4; or the combination of Claim 1+Claim 2+Claim 3+Claim 4; and the like.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent documents, was specifically and individually indicated to be incorporated by reference.

The terms "adapted to," "configured for," and "capable of," mean the same thing. Where more than one of these terms are used in a claim set, it is the case that each and every one of these terms, as they might occur, means, "capable of."

Without implying any limitation, the term "chemical constituent" encompasses chemicals and compounds. "Compound" preferably refers to a molecular entity or complex such as a glycolipid (covalent complex of oligosaccharide and a lipid), a glycopeptide, a lipoprotein, glutamic oxaloacetate amino transferase (complex of an enzyme and pyridoxal phosphate). Where the term "compound" is used, the complex may be a non-covalent complex, it may be a covalent complex, or it may be a complex that has both covalent and non-covalent character. The term "compound" can also be used to the combination of an ionized chemical with its counter ion.

Different botanical products produce different chemical constituents. It is often desirable to extract wanted chemical constituents from unwanted bulk plant material to provide a more well defined, often standardized, extract of components that can be more easily utilized in further processing steps or directly by mammals via various consumption methods. It is always undesirable to utilize extraction methods that may leave unwanted chemical residues in the extract that could limit human consumption potentials. Furthermore, the use of typical solvents like alcohols and alkanes, ethanol and hexane, pose additional flammability and handling hazards which increase the economic burden of the processing method. Certain chemical constituents of interest may be quite polar and could lend towards extraction with water, of which stevia glycosides would be an excellent example, but most often the desired constituents are non-polar and are best extracted via the use of alkanes as the extraction solvent. The present disclosure utilizes vegetable oils as an inexpensive, safe handling and highly efficient means of extracting desired chemical constituents from botanicals of interest.

Figure 2:
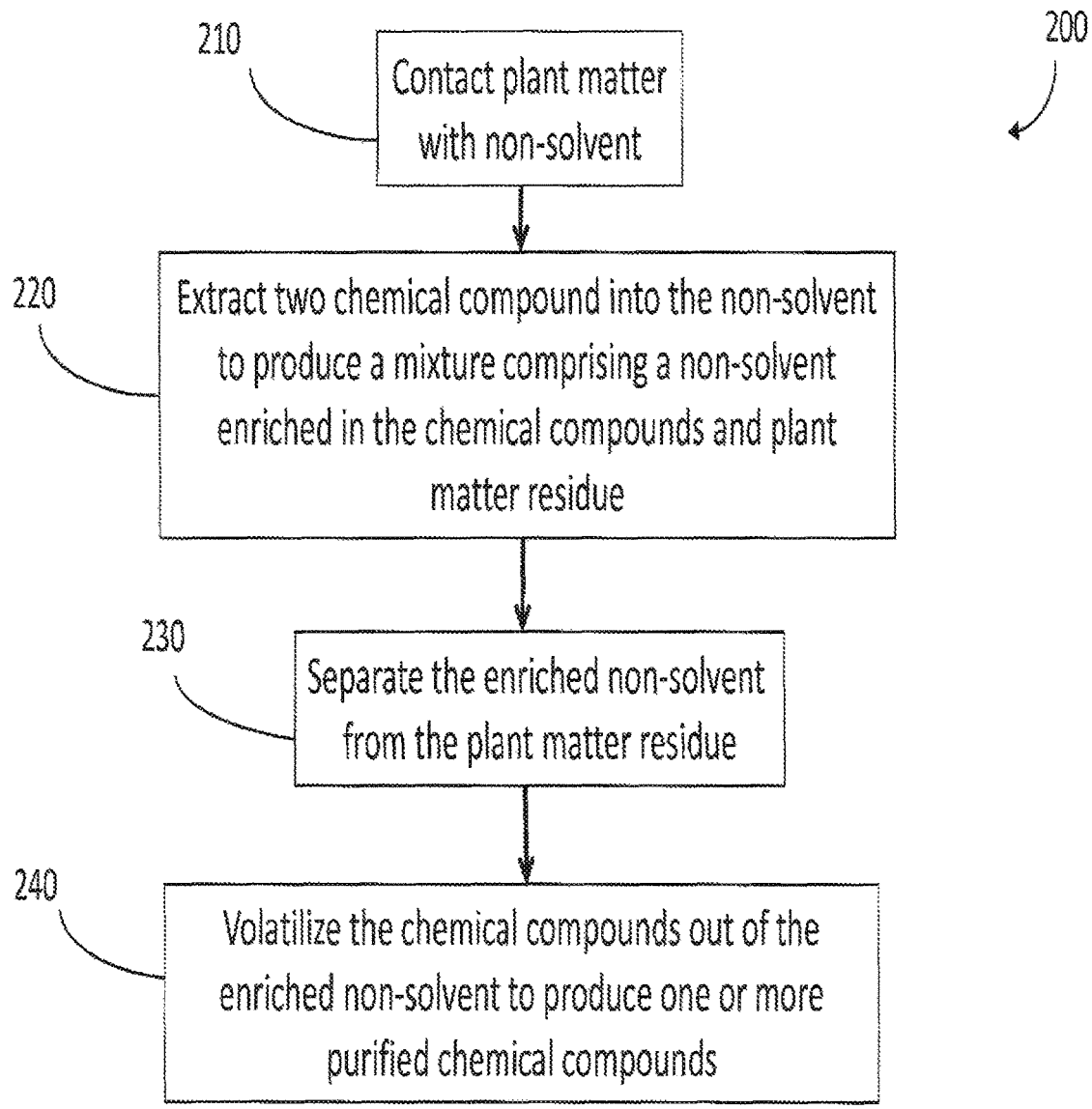
FIG. 2 shows a method of purifying a chemical compound from plant matter.
Figure 3:
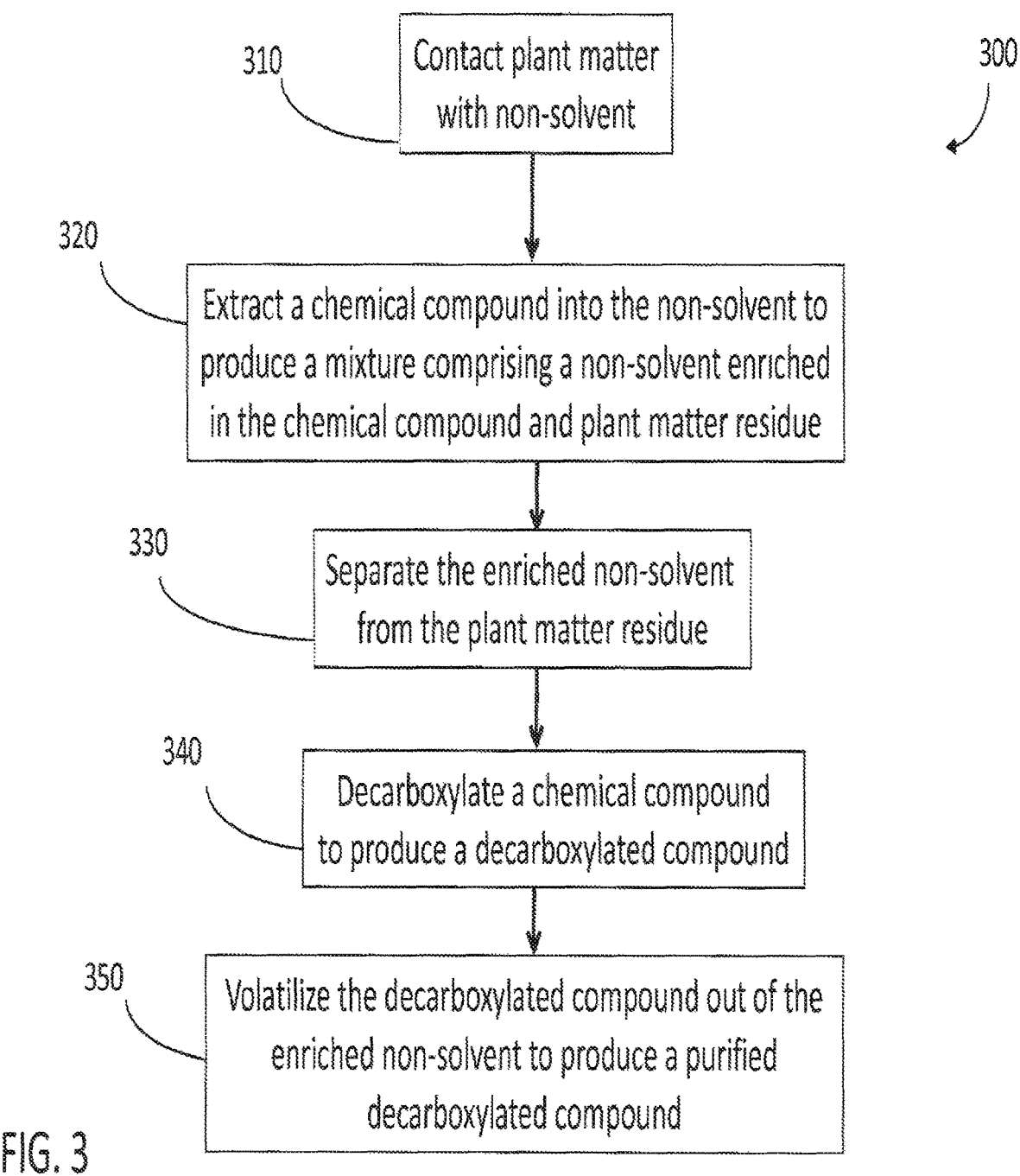
FIG. 3 shows a method of purifying a chemical compound from plant matter.

FIGS. 1-3 show methods of purifying a chemical compound from plant matter according to the present disclosure. The methods described can be performed in the absence of a solvent. The embodiments shown in the figures are non-limiting examples of the methods and processes described herein, and may be modified according to other embodiments described herein. The individual steps of FIGS. 1-3 can be interchanged or combined in accordance with the present disclosure.

FIG. 1 shows a method 100 of purifying a chemical compound. The method can be performed in the absence of a solvent. The method involves an optional first step 110 of distilling a non-solvent to remove a volatile fraction. The non-solvent can comprise an oil such as a plant oil, vegetable oil, seed oil, nut oil, canola oil, fish oil, or the like. In other embodiments, the non-solvent comprises an ionic liquid, such as tributylmethylammonium methyl sulfate. In step 120, the non-solvent, which may have had a volatile fraction removed in step 110, is contacted to plant matter. The plant matter can comprise cannabaceae or a derivative thereof. A chemical compound from the plant matter is extracted into the non-solvent in step 130, producing (1) a mixture comprising a non-solvent enriched in the chemical compound and (2) plant matter residue. The chemical compound may be a carboxylic acid. It may also or alternatively be a cannabinoid. Extraction may involve mixing, stirring, agitating, vortexing, or the like. It may also involve heating. Optionally, the plant matter residue can be further processed in step 135 by contacting it with an aliquot of the non-solvent, and then repeating the extraction step 130. Optionally the mixture can be cooled before proceeding.

The enriched non-solvent and the plant matter residue are separated in step 140. Separating the materials may comprise straining, filtering, or centrifuging. For example, the non-solvent and plant matter mixture can be placed in a food-grade mesh, such as a nylon straining bag, and pressed in a mechanical press, such as a wine press, to separate enriched oil product from plant matter residue byproduct. Alternatively, or in addition, part or all of the mixture can be separated using an auger-type oil extractor. The separating step 140 can be repeated multiple times to extract the most enriched oil product.

Step 150 involves volatilizing the chemical compound out of the enriched non-solvent to produce a purified chemical compound. Volatilizing may comprise exposure to heat, vacuum, or partial vacuum. In a preferred embodiment, heating comprises elevating the temperature over 100 degrees C. In embodiments where the extracted chemical compound is a carboxylic acid, the purified chemical compound may comprise a decarboxylated compound.

FIG. 2 shows a method 200 according to the present disclosure, wherein more than one chemical compound can be purified. The method 200 may embody all of the limitations embodied in the description of the method 100 in FIG. 1. The method 200 further comprises step 220, which involves extracting two or more chemical compounds into the non-solvent to produce a mixture comprising (1) a non-solvent enriched in more than one chemical compound and (2) plant matter residue.

In step 240, one or more chemical compounds are volatilized out of the enriched non-solvent to produce one or more purified chemical compounds. The properties of the compounds may be such that they volatilize at different temperatures. In that case, one compound may be volatilized at a lower temperature, and the second compound may subsequently be volatilized at a higher temperature, leading to two separate purified compounds. The purified compounds may be mixed together or be kept separate. In alternative embodiments, the two compounds may be volatilized at the same time, using a temperature at which both volatilize. The step 240 may result in a volatilized fraction that is enriched in one compound but not the other. Or it may result in a volatilized fraction that is enriched in both compounds. In embodiments, the method 200 may involve more than two compounds with different or the same volatilization temperatures.

FIG. 3 shows another method 300 of purifying a chemical compound. The method 300 involves decarboxylating the chemical compound to produce a decarboxylated compound in step 340. In some embodiments, step 340 occurs in conjunction with a volatilization step 350. In other embodiments, steps 340 and 350 occur separately. The present disclosure encompasses methods wherein step 340 occurs before step 350, as well as methods wherein step 350 occurs before step 340. Decarboxylation may involve heating, such as elevating the temperature of the chemical compound to 100 degrees C. or more. Heating can be by any method known in the art. For example, heating may comprise drawing hot gas through the enriched non-solvent. In other embodiments heating may comprise contacting the non-solvent to a hot surface, such as a surface with a temperature differential of 70 degrees C. compared to the starting temperature of the non-solvent. Heating may also involve the use of an oven or a heat exchanger.

The procedures and processes described below provide a non-limiting and exemplary disclosure of the methods.

Extracting and Filtering

A non-solvent such as canola oil can be purified before use in extracting plant matter, as follows. Canola oil is distilled, and the distillate is set aside or discarded. The non-volatile fraction is retained, for use in extracting plant matter. The non-volatile fraction is mixed with the plant matter, with extraction by stirring for about ten minutes. Preferably, extraction is conducted at 50 degrees C. In various embodiments, extraction can be at about 40° C., about 45° C., about 50° C., about 55° C., about 60° C., about 65° C., about 70° C., about 75° C., where the mixture is held at this temperature for about 5 minutes, about 10 min, about 15 min, about 20 min, about 25 min, about 30 min, about 40 min, about 50 min, about 60 min, about 90 min, and so on. In addition to the above extraction period, the process of extraction can include a ramping-up period, for example, a ten minute period where the temperature of the mixture is ramped up from room temperature to about 50° C. Efficient extraction can be provoked by stirring, sonicating, rocking, tumbling, rotating in a manner that produces a vortex, and so on.

Following extraction, the entire mixture is then strained, for example, using a nylon straining bag, resulting in an oil that is free of visible plant matter. Following extraction and before straining, the mixture is optionally cooled, for example, to room temperature. The once-extracted plant matter can be re-extracted with an unused aliquot of the non-volatile fraction derived from canola oil, resulting in a 2-fold extraction of the plant matter. Alternatively, or in addition, residual extract that is mixed with the plant matter can be removed and collected, using an auger-type oil extruder.

Centrifugation and Heating in Vacuum Oven

After separation from the extracted plant matter, the oil is clarified by centrifuging at 3,000 rpm for ten minutes. The pellet is discarded, and the supernatant is retained. Alternatively, clarification can be at about 3,000 rpm for about 20 minutes, 30 min, 40 min, 60 min, 80 min, 100 min, 120 min, and so on. Also, clarification can be at about 4,000 rpm, 5,000 rpm, 6,000 rpm, 10,000 rpm, for about 20 minutes, 30 min, 40 min, 60 min, 80 min, 100 min, 120 min, and so on. The clarified oil is subjected to heating in a vacuum oven at 115 degrees C., for 710 minutes. The most volatile compounds, such as monoterpenes are removed. Optionally, heating in the vacuum oven is conducted under conditions of temperature and timing that can lead to decarboxylation of THC-acid to THC. Centrifugation can be batchwise or continuous.

For any step in the present disclosure, vacuum can be either a complete vacuum, or a partial vacuum that is 0.9 atmospheres, 0.8, 0.7, 0.6, 0.5, 0.4, 0.3, 0.2, 0.1, 0.05, 0.04, 0.03, 0.02, 0.01, 0.005, 0.004, 0.003, 0.002, 0.001, 0.005, 0.0004, 0.0003, 0.0002, 0.0001, 0.00005, 0.00004, 0.00003, 0.00002, 0.00001 atmospheres, and so on.

Distilling Step and Re-Distilling Step

Following vacuum oven treatment, the oil is then subject to distillation under a vacuum. Distillation is conducted at 175 degrees C., or less, in order to provide the final product of interest. In various embodiments, distillation is at about 140° C., about 145° C., about 150° C., about 155° C., about 160° C., about 165° C., about 170° C., about 175° C., about 180° C., about 185° C., about 190° C., about 200° C., and so on. In exclusionary embodiments, the present disclosure can exclude any process, or can exclude any step, that involves distillation at a temperature that is above 180° C., about 185° C., above 190° C., above 195° C., above 200° C., above 205° C., above 210° C., and so on.

Non-limiting examples of the final product of interest can be, for example, a cannabinoid rich fraction with a content of about 65-75 percent THC. The final product can be subject to another distillation step, for example, at 165 degrees C., to yield a final product of interest that with a content of about 70-90 percent THC. The re-distilling step can be at about 140° C., about 145° C., about 150° C., about 155° C., about 160° C., about 165° C., about 170° C., about 175° C., about 180° C., about 185° C., about 190° C., about 200° C., and so on.

Depletion of Hentriacontane and of Other Chemical Constituents

With a vacuum oven treatment followed by a distillation step, the desired product is an oil, that is optionally depleted in one or more of pentadecanone, octacosane, hentriacontaine, and eicosane. Depletion of hentriacontaine, for example, can result in a clarified oil that contains less than 80% of that present in the oil immediately prior to vacuum oven treatment, less than 70%, less than 60%, less than 50%, less than 40%, less than 30%, less than 20%, less than 10%, less than 5%, less than 2%, and so on, of that present in the oil immediately prior to vacuum oven treatment. In other embodiments, the product immediately after vacuum oven treatment is depleted in octacosane, to one of the above-disclosed percentages, depleted in pentadecanone, to one of the above-disclosed percentages, depleted in eicosane to one of the above percentages, and any combination thereof. Content can be in terms of percentage that a given chemical has, in terms of weight of the chemical compared to weight of the entire oil. Methods for detecting and quantitating pentadecanone, octacosane, hentriacontaine, and eicosane include, gas chromatography (GC), HPLC, GC-mass spectrometry (GC-MS), gas chromatography-olfactometry (GC-O) (Meyre-Silva et al (1998) Phytomedicine. 5:109-113; Usami et al (2013) J. Oleo Sci. 62:563-570; Kuwayama et al (2008) Forensic Sci. Int. 175:85-92).

Process Steps

Methods of the present disclosure can include one or more of the indicated series of steps. In some embodiments, the ordering of the steps is mandatory, while in other embodiments, the ordering of one or more of the steps can be reversed or changed. Any numbers, including weights, volumes, percentages, and times can be varied to produce desired results, as would be understood by a person having ordinary skill in the art.

Step i. Low-THCA canola oil is contacted to extracted plant matter. The combination is stirred at low heat for 10 minutes.

Step ii. The materials are filtered in a wine press through a fine nylon straining bag, to produce a product and a by-product. The product is a first preparation of canola oil with medium content of THCA, and the by-product is extracted plant matter with residual canola oil.

Step iii. The by-product is processed with an auger-type oil expeller.

Step iv. The product of Step (iii) is a second preparation of medium-THCA canola oil, and the by-product is a dry plant matter pellet that contains less than 5% THCA. In alternate, embodiments, the pellet contains less than 10% THCA, less than 8% THCA, less than 6% THCA, less than 4% THCA, less than 2% THCA, less than 1.0% THCA, or less than 0.5% THCA, and so on.

Step v. The first preparation of canola oil is combined with the medium-THCA content and second preparation of medium-THCA canola oil, where the combination is, "combined medium-THCA canola oil."

The following step (Step vi) is an optional step, where canola oil that already contains a moderate quantity (or moderate concentration) of THCA is mixed with an unextracted plant matter, e.g., *cannabis*, where the result is canola oil that is further enriched in THCA. The canola oil that is further enriched in THCA may be referred to as, "high-THCA canola oil."

Step vi. The medium-THCA canola oil is combined with fresh plant matter (e.g., fresh *cannabis*). The combination is filtered in a wine press through a fine nylon straining bag, resulting in a product that is high-THCA canola oil, and a by-product that is extracted plant matter that contains residual canola oil.

The following step (Step vii) is an optional step.

Step vii. The high-THCA canola oil is subjected to a decarboxylation step, where decarboxylation is provoked by heating in a vacuum oven, by heating with an in-line heat exchanger, or by heating by other relevant methods.

The following step (Step viii) is an optional step.

Step viii. The high-THCA canola oil, where treated with a step dedicated to provoking decarboxylation, or where not treated with a step dedicated to provoking decarboxylation, is optionally further processed by centrifugation to remove small particles and debris. The product resulting from this step is "high-THC canola oil." The present disclosure provides compositions and methods, where canola oil is the non-solvent, where canola oil mixed with another non-solvent is used, or where a non-solvent that does not comprise canola oil is used. For example, the non-solvent can be soy oil, corn oil, sunflower oil, sesame oil, safflower oil, olive oil, any mixture thereof, and the like. The non-solvent may comprise an ionic liquid, such as tributylmethylammonium methyl sulfate. The non-solvent may comprise an imidazolium salt, such as 1-butyl-3-methylimidazolium chloride.

Equipment for Purifying and Detecting Chemical Constituents

Cannabinoids can be separated, purified, analyzed, and quantified by a number of techniques. Available equipment and methods include, e.g., gas chromatography, HPLC (high pressure liquid chromatography, high performance liquid chromatography), mass spectrometry, time-of-flight mass spectrometry, gas chromatography-mass spectrometry (GC-MS), and liquid chromatography-mass spectrometry (LC-MS). Equipment for separation and analysis is available from, e.g., Waters Corp., Milford, Mass.; Agilent, Foster City, Calif.; Applied Biosystems, Foster City, Calif.; Bio-Rad Corp., Hercules, Calif.). Equipment for scaled-up processes include rotary evaporators, heat exchangers, driers, and viscosity processors, and are available from, Buchi Corp., New Castle, Del.; Wolverine Tube, Inc., Decatur, Ala.; GEA Heat Exchangers, 44809 Bochum, Germany; LCI Corp., Charlotte, N.C. Pumps and other equipment are available from Grainger, Inc., Lake Forest, Ill. The methods, equipment, and compositions of the present disclosure can include, or be manufactured with, expelling oil with an auger-type oil expeller, drying, and pelleting. Oil expellers are available, e.g., from IBG Monforts Oekotec, Nordrhein-Westfalen, Germany; and Nebraska Screw Press, Lyons, Nebr.

The present disclosure provides in-line monitoring of purification, that is, quantitation of THC as well as quantitation of impurities. In-line monitoring may be by UPLC methods, or by other methods. Ultra-high performance liquid chromatography (UPLC) is similar to HPLC, except that UPLC uses smaller particles in the column bed, and greater pressures. The particles can be under 2 micrometers in diameter, and pressures can be nearly 15,000 psi. UPLC also uses higher flow rates, and can provide superior resolution and run times in the range of under 30 seconds (Wren and Tchelitcheff (2006) J. Chromatography A. 1119:140-146; Swartz, M. E. (May 2005) Separation Science Redefined). The application of UPLC to cannabinoids has been described (see, e.g., Jamey et al (2008) J. Analytical Toxicology. 32:349-354; Badawi et al (2009) Clinical Chemistry 55:2004-2018). Suitable UPLC columns for cannabinoid analysis include, e.g., Acquity® UPLC HSS T3 C18 (100 mm×2.1 mm, 1.8 micrometers), and Acquity® UPLC BEH C18 column (100 mm×2.1 mm, 1.7 micrometers) (Waters, Milford, Mass.). Other methods for detecting cannabinoids include, e.g., infrared (IR) spectroscopy, gas chromatography mass spectroscopy (GCMS), and electrospray tandem mass spectroscopy (ESI-MS/MS) (Ernst et al (2012) Forensic Sci. Int. 222:216-222).

Crude Extracts

The present disclosure provides use of various forms of other botanical extraction products initially made by other extraction methods. Other extraction methods may involve a solvent, such as butane, hexane, methanol, alcohol, water or non-solvent based sub-critical $CO_2$, or super-critical $CO_2$ or other gas in a similar critical-type extraction method. These methods of extraction remove chemical constituents from the plant materials, for example, a mixture of both desired chemicals and non-desired chemicals, where the removed substance takes the form of an oil that typically, is a viscous oil. The resulting oil can be diluted into vegetable oil, and then be processed by a distillation apparatus.

Carbon dioxide is in its supercritical fluid state when both the temperature and pressure equal or exceed the critical point of 31 degrees C. and 73 atmospheres. In its supercritical state, $CO_2$ has both gas-like and liquid-like qualities, and it is this dual characteristic of supercritical fluids that provides the ideal conditions for extracting compounds with a high degree of recovery in a short period of time. Supercritical fluid extraction devices are available from, e.g., Natex Prozesstechnologie, 2630 Ternitz, Austria; Jasco Analytical Instruments, Easton, Md.; Supercritical Fluid Technologies, Inc., Newark, Del.

Without implying any limitation, the ratio (dry wt./dry wt.) of the non-solvent/plant matter, immediately prior to extraction of the plant matter, is greater than 100/1 (dry wt./dry wt.), or about 100/1 (dry wt./dry wt.), 90/1, 80/1, 70/1, 60/1, 50/1, 40/1, 30/1, 20/1, 15/1, 10/1, 9/1, 8/1, 7/1, 6/1, 5/1, 4/1, 3/1, 2/1, 1/1, and so on. In embodiments, the ratio (dry wt./dry wt.) of the non-solvent/plant matter, immediately prior to extraction of the plant matter, is about 1/0.9, 1/0.8, 1/0.7, 1/0.6, 1/0.5, 1/0.4, 1/0.3, 1/0.2, 1/0.1 and so on. Also encompassed, are ratio ranges, such as the range of non-solvent/plant matter from 20/1 to 5/1, or the range of non-solvent/plant matter from 2/1 to 1/0.5.

Methods of the present disclosure can begin with an extract from plant matter, such as a plant that is a member of the cannabaceae, for example, *cannabis*. Where the extract is from *cannabis*, and where the *cannabis* was extracted with canola oil, the result is a high THC canola oil. The high THC canola oil is then subject to distillation, such as bulk distillation, resulting in various fractions. These fractions may include a fraction that is greater than 70% THC, a low THC fraction in canola oil, and a medium THC fraction in canola oil. In this method, the medium THC fraction in canola is subject to an additional round of distillation, in order to obtain a fraction that is high in THC and depleted in canola oil.

Purified Compounds

The present disclosure provides by way of example only and not implying any limitation in any way, methods for purifying cannabinoids including specific temperatures, timing, and so on. Methods for purifying the following cannabinoids, without limitation, are provided by the present disclosure. Some examples of cannabacea, and their classification, are as follows: *Aphananthe* Planchon (syn. *Mirandaceltis* Sharp); *Cannabis* L.; *Celtis* L. (hackberries) (syn, Sparrea Hunz. & Dottori); *Gironniera gaudich.* (syn. *Helminthospermum thwaites, Nematostigma* Planchon); *Humulus* L. (hops) (syn. *Humulopsis. grudz.*); *Lozanella* Greenman; *Parasponia* Miguel; *Pteroceltis* Maxim; *Trema* Loureiro (syn. *Sponia decaisne*); *Lozanella; Parasponia; Pteroceltis*. The present disclosure provides methods for purifying compounds and chemicals from each of these cannabaceae. The disclosure also provides purified chemical constituents, chemical compositions, compounds, and chemicals, that are prepared by these methods.

The disclosure provides chemical compositions that comprise cannabinoids, that comprises cannabinoids but not terpenes, that comprise terpenes but not cannabinoids, and the like. Without implying any limitation, the present disclosure encompasses a method where terpenes are volatilized at a lower temperature, in order to separate terpenes from cannabinoids, followed by increasing the temperature to volatilize cannabinoids, in order to produce a batch of terpenes and a batch of cannabinoids. In another method, both terpenes and cannabinoids are first volatilized together at a higher temperature, followed by collecting the batch that contains both terpenes and cannabinoids, followed by separating the terpenes from the cannabinoids, e.g., by heating.

"Plant matter that is derived from cannabaceae" refers, without implying any limitation, to freshly harvested cannabaceae, sun-dried cannabaceae, chopped cannabaceae, ground cannabaceae, powdered cannabaceae, cannabaceae that is dried and chopped or ground or powdered (where drying is before or after being chopped, ground, or powdered), cannabaceae that comprises fungus or mold, and so on.

Where a chemical composition does not comprise cannabinoids, this can refer to a chemical composition where less than 5.0%, less than 2.0%, less than 1.0%, less than 0.5%, less than 0.2%, less than 0.1%, less than 0.05%, less than 0.02%, less than 0.01%, less than 0.005%, less than 0.002%, less than 0.001%, less than 0.0005%, less than 0.0002%, less than 0.0001%, and so on (by weight), are cannabinoids. Where a chemical composition does not comprise terpenes, this can refer to a chemical composition where less than 5.0%, less than 2.0%, less than 1.0%, less than 0.5%, less than 0.2%, less than 0.1%, less than 0.05%, less than 0.02%, less than 0.01%, less than 0.005%, less than 0.002%, less than 0.001%, less than 0.0005%, less than 0.0002%, less than 0.0001%, and so on (by weight), are terpenes.

General chemical reagents, as well as cannabinoids, are available (Sigma Aldrich, St. Louis, Mo.; Fischer Chemicals, Fair Lawn, N.J.; Cerilliant, Round Rock, Tex.; Promochem, Molsheim, France, Cayman Chemical Co., Ann Arbor, Mich.). Purification can be followed by spiking an extract with a labeled cannabinoid. Useful labels include 33P, 35S, 14C, 3H, stable isotopes, fluorescent dyes, or fluorettes (see, e.g., Rozinov and Nolan (1998) Chem. Biol. 5:713-728).

Heat-Induced Decarboxylation

Decarboxylation of cannabinoids can be induced by heating. Cannabinoid acids can decarboxylate to the corresponding cannabinoids. For example, cannabidiolic acid can decarboxylate to produce cannabidiol (Veress, et al (1990) J. Chromatography A. 520:339-347; Jung et al (2007) J. Mass Spectrom. 42:354-360; Harvey (1990) J. Ethnopharmacol. 28:117-128). Alkaline conditions can accelerate the heat-induced decarboxylation of cannabinoid acids (Auwarter et al (2010) Forensic Sci. Int. 196:10-13). Contacting *cannabis* biomass with gas at a temperature of 105-450 degrees C., and in particular at 105-225 degrees C., can provoke decarboxylation of cannabinoid acids to free cannabinoids. At 145 degrees C., for example, about 95% of cannabinoid acid is decarboxylated in about 30 minutes. Lower temperatures can be chosen to avoid thermal oxidation of delta-9-tetrahydrocannabinol (delta-9-THC) to CBN, and thermal isomerization of delta-9-THC to delta-8-tetrahydrocannabinol (delta-8-THC).

Cannabinoids that can be decarboxylated include THCA (to THC), CBGA (to CBG), and CBDA (to CBD). In one aspect of the disclosure, THCA decarboxylation is at least 50%, at least 60%, at least 70%, at least 80%, at least 90%, at least 95%, at least 98%, at least 99%, at least 99.5%, at least 99.9%, and the like. In another aspect, CBGA decarboxylation is at least 1%, at least 10%, at least 20%, at least 30%, at least 40%, at least 50%, at least 60%, at least 70%, at least 80%, at least 90%, at least 95%, at least 98%, at least 99%, at least 99.5%, at least 99.9%, and so on.

In a non-limiting embodiment, the present disclosure volatilizes one or more chemical constituents, such as cannabinoids, at a temperature of 80-85 degrees C., 85-90 degrees C., 90-95 degrees C., 95-100 degrees C., 100-105 degrees C., 105-110 degrees C. 110-115 degrees C., 115-120 degrees C., 120-125 degrees C., 125-130 degrees C., or at a temperature of 80-90 degrees C., 85-95 degrees C., 90-100 degrees C., 95-105 degrees C., 100-110 degrees C., 105-115 degrees C., 110-120 degrees C., 115-125 degrees C., 120-130 degrees C., and so on. In exclusionary embodiments, the present disclosure excludes any method that volatilizes chemical constituents at above 95 degrees C., at about 98 degrees C., at above 100 degrees C., at above 103 degrees C., at above 105 degrees C., at above 108 degrees C., at above 110 degrees C., and so on.

Without implying any limitation, the present disclosure encompasses a method that involves contacting a chemical constituent to a matrix, and contacting a hot gas to the matrix, resulting in volatilizing one or more chemical constituents from the matrix. The matrix can comprise, for example, one or more of a porous ceramic, hollow fibers, glass wool, glass beads, celite, and the like. In exclusionary embodiments, the present disclosure can exclude any method, and any chemical constituent prepared by the method, that involves contacting a chemical constituent to a matrix. What can be excluded is any method that involves contacting an extract with a matrix, resulting in a matrix that is coated with the extract, and contacting a hot gas to the coated matrix, resulting in volatilizing one or more chemicals or more or more chemical constituents from the matrix.

In hot gas embodiments, the present disclosure encompasses one gas, such as nitrogen, argon, carbon dioxide, helium, atmospheric air, water vapor, for use, for example, volatilizing a chemical constituent. Alternatively, the disclosure encompasses two hot gases such as a mixture of nitrogen and carbon dioxide, nitrogen and water vapor, carbon dioxide and water vapor, atmospheric air and nitrogen, atmospheric air and carbon dioxide, atmospheric air an argon, for example, for volatilizing a chemical constituent. In another embodiment, the disclosure encompasses three or more gasses, for example, for volatilizing a chemical constituent.

In exclusionary embodiments, the present disclosure can exclude one gas, such as nitrogen, argon, carbon dioxide, helium, atmospheric air, water vapor, for use, for example, volatilizing a chemical constituent. Alternatively, the disclosure can exclude two hot gases such as a mixture of nitrogen and carbon dioxide, nitrogen and water vapor, carbon dioxide and water vapor, atmospheric air and nitrogen, atmospheric air and carbon dioxide, atmospheric air an argon, for example, for volatilizing a chemical constituent. In another embodiment, the disclosure can exclude three or more gasses, for example, for volatilizing a chemical constituent.

By way of a non-limiting example, dry and homogenized *cannabis* can be extracted with methanol:chloroform (9:1, vol./vol.), and then subject to decarboxylation, by the following procedure. Dry and homogenized *cannabis* can be extracted in the solvent by vortexing, followed by sonication in an ultrasonic bath, with repetition of the vortexing procedure after 5 minutes, after 10 minutes, and again after 15 minutes. Solid plant matter can then be separated from the extract by centrifugation. Decarboxylation can be accomplished as follows. The resulting oil can then be decarboxylated by heating at 210 degrees C. for 15 minutes.

Decarboxylation Induced During Heat-Induced Vaporization

Cannabinoid acids present in a non-solvent extract can be decarboxylated by a hot gas, with vaporization of the decarboxylated cannabinoids. Alternatively, cannabinoid acids present in the mixture of non-solvent extract and plant matter can be decarboxylated by a hot gas, with vaporization of the decarboxylated cannabinoids. In heat-induced vaporization, a hot gas is bubbled through the extract (or mixture of plant matter and the non-solvent) resulting in decarboxylation and vaporization. The gas can be, for example, atmospheric air, nitrogen, argon, or any combination thereof. The temperature of the gas can be, for example, less than 100 degrees C., 100-110 degrees C., 110-130 degrees C., 130-150 degrees C., 150-170 degrees C., 170-190 degrees C., 180-200 degrees C., 190-210 degrees C., 200-220 degrees C., 210-230 degrees C., 220-240 degrees C., 230-250 degrees C., 240-260 degrees C., and so on. Following bubbling, the vapor can be bubbled through a second non-solvent that has a controlled, cool temperature, in order to collect the decarboxylated cannabinoids. This method of heat-induced decarboxylation, when carried out with the mixture of non-solvent extract and plant matter, can avoid steps of centrifugation, filtering, or both centrifugation and filtering that are needed to remove extracted plant matter and other solid residues.

Decarboxylation can be achieved by contacting the extract containing cannabinoid acids with a hot surface. For example, decarboxylation occurs when contacting an enriched non-solvent vegetable oil solution to a surface with a temperature of 70 degrees C. higher than the solution for a period of 60 minutes. In other embodiments, the temperature differential can be higher than 80 degrees C., higher than 90 degrees C., higher than 100 degrees C., higher than 110 degrees C., higher than 120 degrees C., higher than 130 degrees C., higher than 140 degrees C., or higher than 150 degrees C. Contact times with the hot surface can be about 1 minute, 2 minutes, 5 minutes, 10 minutes, 15 minutes, 30 minutes, 60 minutes, 90 minutes, 120 minutes, or the like.

Other methods of decarboxylation involve the use of an oven or other heating apparatus. Higher heat generally equates to a faster rate of decarboxylation.

Lipid Compositions

The present disclosure provides non-solvent lipid compositions for use as an extraction agent, for use as a carrier, or for use as both an extraction agent and as a carrier, for processing chemical constituents and for serving as a vehicle for dissolving said chemical constituents. The lipid composition can be, canola oil, peanut oil, sunflower oil, safflower oil, corn oil, soy oil, sesame oil, olive oil, avocado oil, grapeseed oil, mulatto oil, almond oil, mustard oil, walnut oil, seed oil, nut oil, ground nut oil, a tree oil, jojoba oil, guayule oil, fish oil, cod liver oil, oil from a recombinant plant or from a recombinant microorganism, or any combination thereof, and the like. Also available, is an oil such as a wax oil, that is not a triglyceride oil. Moreover, the lipid composition can be a fat that is normally a solid at room temperature, and where extraction occurs at or above the melting temperature of the fat. The fat can be, for example, butter, margarine, lard, hydrogenated vegetable oil, partially hydrogenated vegetable oil, any combination thereof, and the like. Furthermore, the lipid composition can be a combination of an oil and a fat, such as a combination of canola oil and butter. What is encompassed is plant-derived oils, fungus-derived oils, animal-derived oils, microorganism-derived oils, oils manufactured by recombinant microorganisms or recombinant algae and the like.

Prior to use, the carrier lipid composition is subject to a purification scheme. Purification can be accomplished with distilling under vacuum (0.001 mbar) at higher temperatures (195 degrees C.). Preferred vacuum is a vacuum of 0.001 torr, or a more intense vacuum, Regarding units, it is the case that 1 mbar equals 0.750 torr. A goal is to ensure that the chemical constituents provided by the present methods and systems do not contain residues from the vegetable oil, or from any other lipid composition that is used. The method keeps the highest boiling portions to use for the extraction, as these portions need to be higher in boiling point than the chemical constituents of interest in and on the plant.

In an alternative embodiment, distillation is conducted at atmospheric pressure (and not under any partial vacuum). Atmospheric pressures for distillation can lead to the ability to select alternative fractionates where it is desired to only fractionate out light boiling chemical constituents.

In exclusionary embodiments, the present disclosure can exclude any system, method, and composition, that involves a solvent, a solvent that is at least 95% pure, a solvent that is at least 99% pure, and the like, such as acetone, an ether, dimethyl ether, diethyl ether, an alcohol, methanol, ethanol, propanol, isopropanol, methylene chloride, chloroform, or any combination thereof, and so on. In exclusionary embodiments, what can also be excluded is any system, method, and composition, prepared with the use of butter, margarine, lard, fish oil, hydrogenated vegetable oil, partially hydrogenated vegetable oil, and the like. In other exclusionary embodiments, what can be excluded is any system, method, or composition, that is prepared with or that contains, a seed oil, a nut oil, a ground nut oil, a tree nut oil, canola oil, peanut oil, sunflower oil, safflower oil, corn oil, soy oil, sesame oil, olive oil, or any combination thereof, and the like.

What can be excluded is an extraction procedure, where extraction is with a mixture of solvent and non-solvent. Also, what can be excluded is an extraction procedure, where extraction with a solvent is followed by extraction with a non-solvent, or where extraction with a non-solvent is followed by extraction with a solvent. What can be excluded, for example, is an extraction procedure where extraction is with vegetable oil/methanol (10%/90%) vegetable oil/methanol (20%/80%) by weight), vegetable oil/methanol (40%/60% by weight), vegetable oil/methanol (50%/50% by weight), vegetable oil/methanol (80%/20% by weight), vegetable oil/methanol (90%/10% by weight), and so on.

What can be excluded, for example, is an extraction procedure where extraction is with vegetable oil/methylene chloride (20%/80% by weight), vegetable oil/methylene chloride (40%/60% by weight), vegetable oil/methylene chloride (50%/50% by weight), vegetable oil/methylene chloride (80%/20% by weight), vegetable oil/methylene chloride (90%/10% by weight), and so on.

Also provided, is an extraction procedure that uses a non-solvent such as canola oil, where the extraction is with a liquid that is a mixture of non-solvent and solvent. The mixture can take the form, on a percent weight basis, of about 95% non-solvent/5% solvent, about 90% non-solvent/10% solvent, about 85% non-solvent/15% solvent, about 80% non-solvent/20% solvent, about 75% non-solvent/25% solvent, about 70% non-solvent/30% solvent, and the like. The above methods and mixtures can also be exclusionary.

Location of the Step of Heat-Induced Decarboxylation in the Process Scheme

Heat-induced decarboxylation can be performed on non-extracted plant matter. However, it is preferred to perform heat-induced decarboxylation on the non-solvent extract, because the extract has a smaller volume than the plant matter, and also because the presence of plant matter is expected to generate off-flavors or off-odors. Heat-induced decarboxylation is preferably conducted before distillation (or other process step involving pressure and heating), because any decarboxylation that occurs inside a distillation apparatus could disrupt the vacuum, resulting in inefficient distillation, for example, taking the form of bumping.

Recovery

One hundred percent (100%) of cannabinoids can be defined as the total amount, in terms of moles, that is initially present in the non-extracted plant matter. Alternatively, 100% can be defined as the total amount, in terms of moles, that is initially present in the non-solvent extract. In yet another alternative, 100% can be defined as the total amount, in terms of moles, that is present at the beginning of any given process step. In a preferred embodiment, the final product of the present disclosure takes the form of a cannabinoid-rich resin. This cannabinoid-rich resin can optionally be redistilled to achieve higher purity. Redistillation is preferably at 165 degrees C., where the result is a resin containing THC at a purity of greater than 80%.

Reductions in the proportion of non-solvent, such as a vegetable oil, are desired. Inhaled vegetable oils can result in a disorder called, "exogenous lipoid pneumonia" (Annobil et al (1997) Trop. Med. Int. Health. 2:383-388; Hoffman et al (2005) Arch. Pediatr. Adolesc. Med. 159:1043-1048; Betancourt et al (2010) Am. J. Roentgenol. 194:103-109).

In embodiments, cannabinoid purity is greater than 70%, greater than 75%, greater than 80%, greater than 85%, greater than 90%, greater than 95%, greater than 96%, greater than 97%, greater than 98%, greater than 99%, greater than 99.5%, where the percent can be in terms of weight of cannabinoid as a percentage of weight of the resultant oil, where the percent of cannabinoid can be in terms of moles of cannabinoid molecules as a percentage of moles of the total molecules.

Recovery of the cannabinoids can be measured after each process step. Where applicable, recovery can also be measured after each reiteration of a process step that is repeated.

Overall recovery can refer to the difference between the number of moles of cannabinoids that is initially extracted with the non-solvent extracting reagent, and the final purified product. Alternatively, overall recovery can refer to the difference between the number of moles of cannabinoids in the non-extracted plant matter, and the final purified product.

In embodiments, the overall recovery can be at least 99%, at least 98%, at least 97%, at least 96%, at least 95%, at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, at least 10%, and the like. Where aliquots of sample are withdrawn from the process, at one or more steps, the recovery is corrected for the amount withdrawn. Aliquots can be withdrawn for analysis, for quality control, or for storage.

An alternative method for calculating recovery, is to factor in a reduction in recovery, where one or more cannabinoids have been found to be converted to a non-desirable entity, such as to a cannabinoid that is isomerized, oxidized, oxidized to create an aldehyde, ring opened, condensed with another *cannabis*-derived chemical constituent, condensed with a component of the non-solvent extracting agent, or otherwise destroyed. In other words, where 5% of the moles of cannabinoid have been found to be oxidized to an aldehyde, the calculated recovery can be proportionately reduced.

Rate-Limiting Step

The present disclosure provides a multi-step processes that avoids, or reduces, the tendency of any given step to be a rate-limiting step. For example, in a multi-step process that processes 100 grams of cannabinoid per hour (overall production, as measured immediately after the final step), the process can be operated to minimize accumulation of cannabinoids immediately before a given intermediate step that is identified as potentially a rate-limiting step. The methods of the present disclosure can be adjusted, to minimize accumulation of cannabinoids immediately before the potential rate-limiting step at under 20 grams cannabinoid per hour, under 15 grams, under 10 grams, under 5 grams, under 4 grams, under 3 grams, under 2 grams, under 1 gram, under 0.5 grams, under 0.2 grams, under 1 gram, under 0.5 grams, under 0.2 grams, under 0.1 grams, and so on. As stated above, this is with regard to a multi-step process that produces a composition at a rate of 100 grams of cannabinoid per hour. In non-limiting embodiments, this 100 grams of cannabinoid may be at least 70% pure, at least 80% pure, at least 90% pure, at least 95% pure, at least 98% pure, and so on.

The term "accumulation" refers to cannabinoid that piles up immediately before that step, resulting in a delay or hold-up of flow of chemical constituents through subsequent steps. Expressed another way, the method maintains a ceiling of cannabinoid accumulation at under 20%, under 15%, under 10%, under 5%, under 2%, under 1%, under 0.5%, under 0.2%, under 0.1%, and so on, with respect to the "100%" that is defined above, To repeat, the term "accumulation" does not refer to the total amount of cannabinoid that passes through a given step per hour, but instead, it refers to the amount that piles up at that given step, resulting in a slight delay (or perhaps in a more lengthy delay) in processing of the cannabinoid through subsequent steps.

Exclusionary Embodiments

Without implying any limitation, the present disclosure can exclude any method that extracts plant matter with an alcohol (e.g., methanol, ethanol, isopropanol), that extracts plant matter with supercritical fluid carbon dioxide, that extracts plant matter with a non-aqueous solvent, that extracts plant matter with, e.g. dichloromethane, hexane, ether, and so on. What can also be excluded is any method that uses a cyclone separator, or any method where heat-induced decarboxylation is performed on non-extracted plant matter, or where heat-induced decarboxylation is performed prior to extraction of plant matter.

Processes

Following removal of the spent plant matter, the extract can be heated in order to provoke heat-induced decarboxylation of cannabinoids. Alternatively, the step of heating can be carried out at an earlier pan of the scheme, where the extract is subjected to beating in order to volatilize the cannabinoids, where decarboxylation occurs during this heating, and where the volatilized cannabinoids are then captured using a condenser. In a preferred but non-limiting embodiment, the volatilized cannabinoids are condensed and captured by drawing through canola oil, where the canola oil is at or below room temperature. Once captured, the cannabinoids can be: (1) Considered to be the final product, (2) The cannabinoids can be dispersed into a non-solvent such as canola oil and then optionally subjected to further purification, or (3) The cannabinoids can be subject to further purification. At the end of the process, the used canola oil can be utilized again for extracting plant matter.

In one embodiment, the starting material is canola oil that has a high content of THC. The high-THC canola oil is optionally subjected to distillation. Immediately after processing by the distillation step, the products are medium-THC canola oil, low-THC canola oil, and a THC-composition that is greater than 50% THC. The medium-THC canola oil can be re-processed by distillation.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant.

In this regard it should be understood that for practical reasons and so as to avoid adding potentially hundreds of claims, the applicant has presented claims with initial dependencies only.

Support should be understood to exist to the degree required under new matter laws—including but not limited to 35 USC § 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

While the system, compositions, and methods, have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

Example 1

The following example outlines a decarboxylation trial performed using the methods and systems of the present disclosure. The goal of the trial was to decarboxylate THCA to THC at 145 degrees C. for 10 minutes exposure time. An in-line decarboxylation pipe with a total internal surface area was approximately 46.8 $in^2$ was utilized.

A pump drive forces the material of interest, such as THCA-enriched canola oil, through the apparatus at a rate of 10 mL/min. The apparatus was heated with heating fluid of constant temperature. For the present trial, the heating fluid was set to 200 degrees C. Thermocouples at the inlet and outlet measured the temperature of the material of interest before decarboxylation and after. The average inlet temperature was 77.2 degrees C., and the average outlet temperature was 149.3 degrees C., as measured by the thermocouples.

The collection vessel was situated on a stir plate, so that stirring could be used to ensure homogeneity of the collected solution.

An initial volume of 250 mL of THCA-enriched canola oil was transferred to the collection vessel. The material was measured for THC and THCA prior to decarboxylation. The starting level of THC was 21.91 mg/g; and the starting level of THCA was 11.05 mg/g. The material was recirculated through the apparatus at the rate of 10 mL/min as determined by the pump. Each theoretical pass of 250 mL through the apparatus therefore required 25 minutes.

THC and THCA levels in the material were measured at intervals of 25-30 minutes. At each interval, a sample of material was taken directly from the outlet. In addition to the initial measurement at t=0, twelve theoretical passes were measured, for a total experiment time of approximately 354 minutes. The experimental results are displayed in Table 1 and in the corresponding graph in FIG. 4.

TABLE 1

| Sample | Time (m) | THC % | THCA % | CBN % | Unk.Deg. % | THC [mg/g] | THCA [mg/g] | % Decarbed |
|---|---|---|---|---|---|---|---|---|
| 1 | 0 | 2.191 | 1.105 | 0.216 | 0.215 | 21.91 | 11.05 | 49.56 |
| 2 | 29 | 2.707 | 0.076 | 0.211 | 0.276 | 27.07 | 0.76 | 97.19 |
| 3 | 58 | 2.844 | 0 | 0.213 | 0.267 | 28.44 | 0 | 100 |
| 4 | 87 | 2.867 | 0 | 0.227 | 0.292 | 28.67 | 0 | 100 |
| 5 | 116 | 2.979 | 0 | 0.238 | 0.27 | 29.79 | 0 | 100 |
| 6 | 150 | 3.041 | 0 | 0.244 | 0.288 | 30.41 | 0 | 100 |
| 7 | 176 | 3.117 | 0 | 0.252 | 0.276 | 31.17 | 0 | 100 |
| 8 | 205 | 3.18 | 0 | 0.256 | 0.241 | 31.8 | 0 | 100 |
| 9 | 234 | 3.151 | 0 | 0.273 | 0.259 | 31.51 | 0 | 100 |
| 10 | 260 | 3.185 | 0 | 0.275 | 0.26 | 31.85 | 0 | 100 |
| 11 | 291 | 3.067 | 0 | 0.28 | 0.253 | 30.67 | 0 | 100 |
| 12 | 325 | 3.159 | 0 | 0.295 | 0.293 | 31.59 | 0 | 100 |
| 13 | 354 | 3.136 | 0 | 0.301 | 0.271 | 31.36 | 0 | 100 |

Figure 4:
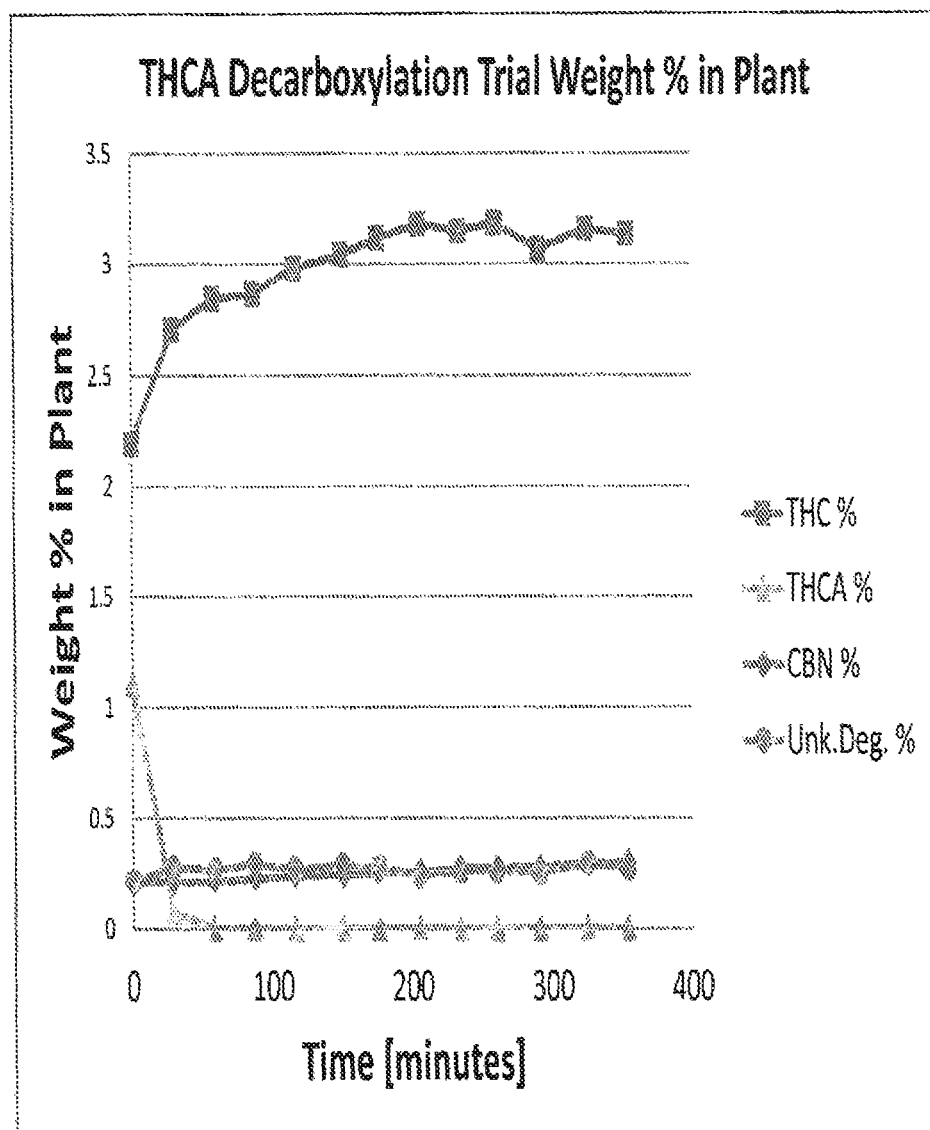
FIG. 4 shows experimental results of a decarboxylation trial according to methods of the present disclosure.

Sample points 2-13 on the graph in FIG. 4 each represent one theoretical run of 25-30 minutes. The first sample point represents the material before it was run through the apparatus. After the first 2 theoretical runs, no concentration of THCA is detected. The absolute maximum THC concentration measured in the experiment occurs after 10 theoretical runs at 260 minutes. The second-highest measured THC concentration was after 7 theoretical runs at 176 minutes.

Example 2

Using an apparatus with greater surface area than the one described in Example 1, it is possible to decarboxylate more efficiently. In another experiment using an in-line decarboxylation pipe having a total internal surface area of 249.6 in$^2$ (or more than 5 times the internal surface area of the device of Example 1), decarboxylation efficiency increases. In this modified apparatus, one theoretical run at 10 mL/min creates 198 seconds of exposure time. Factoring in an estimated 8.25 mL of dead volume in the pipe, one theoretical run creates 49.5 seconds of exposure time.

In the first theoretical run, 97.19% of the THCA was convened to THC. That is about double the efficiency of the device in Example 1, where only 49.56% of THCA was decarboxylated in the first run. The 97.19% decarboxylation equated to 2.367 g of THCA, or 6.602 mmol THCA in 37.2 seconds of exposure time.

What is claimed is:

1. A method for purifying one or more chemical constituents from plant matter; the method comprising:
   (i) contacting the plant matter with a non-solvent to obtain a mixture of extracted plant matter and non-solvent enriched in one or more chemical constituents from the plant matter; and
   (ii) separating the non-solvent enriched in one or more chemical constituents from the extracted plant matter using an auger-type oil extractor;
      wherein the step of separating the non-solvent enriched in one or more chemical constituents comprises drawing hot gas through the non-solvent to obtain a volatilized fraction and a removed fraction.

2. The method according to claim 1, wherein the non-solvent is selected from the group consisting of plant oil, wax oil, fish oil, fruit oil, and a mixture thereof.

3. The method according to claim 1, wherein the non-solvent is tributylmethylammonium methylsulfate or 1-butyl-3-methylimidazolium chloride.

4. The method according to claim 1, wherein the one or more chemical constituents is separated from the non-solvent via volatilization.

5. The method according to claim 4, wherein the step of volatilization results in the separation of a first chemical constituent from a second chemical constituent.

6. The method of claim 4, wherein the step of volatilization results in one or more volatilized fractions.

7. The method according to claim 6, wherein the one or more volatilized fractions is enriched in one or more cannabinoids.

8. The method according to claim 7, wherein the one or more cannabinoids is selected from the group consisting of delta-9 tetrahydrocannabinol, tetrahydrocannabinolic acid, cannabidiol, and cannabinol.

9. The method according to claim 7, wherein volatilization results in the separation of a first cannabinoid from a second cannabinoid.

10. The method according to claim 6, wherein the one or more volatilized fractions is depleted in one or more cannabinoids.

11. The method according to claim 1, wherein the step of separating non-solvent enriched in the one or more chemical constituents comprises centrifugation or filtration.

12. The method according to claim 1, further comprising condensing the volatilized fraction and the removed fraction to obtain a composition comprising the one or more chemical constituents.

13. The method according to claim 1, wherein hot gas induces decarboxylation of at least one heat-decarboxylatable cannabinoid.

14. The method according to claim 1, wherein steps (i)-(ii) are repeated continuously.

15. The method according to claim 1, wherein the plant matter is in a form selected from the group consisting of dried, chopped, ground and powdered.

16. The method according to claim 1, wherein the plant matter is selected from species in the Cannabaceae family.

* * * * *